(12) United States Patent
Yamagata et al.

(10) Patent No.: US 8,834,814 B2
(45) Date of Patent: Sep. 16, 2014

(54) AUTOMATIC ANALYSIS SYSTEM WITH REMOVAL, TRACKING, AND MOUNTING OF STOPPER BODIES

(75) Inventors: Toshiki Yamagata, Hitachinaka (JP); Kenichi Takahashi, Naka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 13/981,337

(22) PCT Filed: Jan. 25, 2012

(86) PCT No.: PCT/JP2012/051557
§ 371 (c)(1),
(2), (4) Date: Aug. 7, 2013

(87) PCT Pub. No.: WO2012/105388
PCT Pub. Date: Aug. 9, 2012

(65) Prior Publication Data
US 2013/0305846 A1    Nov. 21, 2013

(30) Foreign Application Priority Data

Jan. 31, 2011   (JP) ................. 2011-017390

(51) Int. Cl.
*B01L 3/02* (2006.01)
*G01N 1/22* (2006.01)
*G01N 1/00* (2006.01)
*G01N 35/02* (2006.01)

(52) U.S. Cl.
CPC . *G01N 1/00* (2013.01); *G01N 35/02* (2013.01)
USPC ...................................... 422/509; 73/863.01

(58) Field of Classification Search
CPC ... G01N 35/04; G01N 35/10; G01N 2035/04; G01N 2035/0496; G01N 2035/00792; G01N 2035/00811

USPC ........................................ 422/509; 73/863.01
See application file for complete search history.

(56) References Cited

U.S. PATENT DOCUMENTS 5,846,489 A * 12/1998 Bienhaus et al. ................ 422/63
6,077,481 A *  6/2000 Ichida et al. ..................... 422/65
(Continued)

FOREIGN PATENT DOCUMENTS

EP      2031407 A1 * 3/2009 ............. G01N 35/04
JP      03-186354 A      8/1991
(Continued)

OTHER PUBLICATIONS

International Preliminary Report on Patentability received in International Application No. PCT/JP2012/051557 dated Aug. 15, 2013.

*Primary Examiner* — Hezron E Williams
*Assistant Examiner* — Nathaniel Kolb
(74) *Attorney, Agent, or Firm* — Mattingly & Malur, PC

(57) ABSTRACT

The automatic analysis system is equipped with a mechanism to transport a sample container having a stopper body, the system comprising: a sample dispensing mechanism that dispenses a predetermined amount of sample accommodated in the sample container; a stopper body removing/mounting mechanism that removes the stopper body from the sample container; a control unit that stores therein association between the sample container and the stopper body of the sample container; the stopper body removing/mounting mechanism that in accordance with the association stored into the control unit, mounts the stopper body back on the sample container containing the sample dispensed by the sample dispensing mechanism; and a stopper body transport mechanism that transports the sample that the stopper body removing/mounting mechanism has removed at a stopper removing position to a stopper mounting position.

10 Claims, 29 Drawing Sheets

(56) References Cited

U.S. PATENT DOCUMENTS

| | | | | |
|---|---|---|---|---|
| 6,141,602 A | * | 10/2000 | Igarashi et al. | 700/226 |
| 6,216,340 B1 | * | 4/2001 | Fassbind et al. | 29/773 |
| 6,227,053 B1 | * | 5/2001 | Purpura et al. | 73/627 |
| 6,347,552 B1 | * | 2/2002 | Purpura et al. | 73/633 |
| 8,562,909 B2 | * | 10/2013 | Schacher | 422/63 |
| 8,685,321 B2 | * | 4/2014 | Deppermann et al. | 422/65 |
| 2001/0013169 A1 | * | 8/2001 | Fassbind et al. | 29/773 |
| 2008/0047369 A1 | | 2/2008 | Tsujimura et al. | |
| 2010/0018330 A1 | * | 1/2010 | Marty et al. | 73/864.81 |
| 2011/0088517 A1 | * | 4/2011 | Tsujimura et al. | 81/3.09 |
| 2011/0195866 A1 | * | 8/2011 | Deppermann et al. | 506/12 |
| 2012/0321516 A1 | * | 12/2012 | Schacher | 422/68.1 |

FOREIGN PATENT DOCUMENTS

| | | | | |
|---|---|---|---|---|
| JP | 07-031890 A | 2/1995 | | |
| JP | 08-094624 A | 4/1996 | | |
| JP | 11-094841 A | 4/1999 | | |
| JP | 2955613 A | 7/1999 | | |
| JP | 11-304809 A | 11/1999 | | |
| JP | 2000-046837 A | 2/2000 | | |
| JP | 2003-098179 A | 4/2003 | | |
| JP | 2005-271991 A | 10/2005 | | |
| JP | 2007-309675 A | 11/2007 | | |
| JP | 2008-051531 A | 3/2008 | | |
| JP | 2009-036511 A | 2/2009 | | |
| WO | WO 2009141957 A1 | * | 11/2009 | G01N 35/04 |

* cited by examiner (A) FLOW OF DESTOPPERING (1) GRIP THE SAMPLE CONTAINER THAT HAS ARRIVED (2) LIFT THE SAMPLE CONTAINER TO DESTOPPERING POSITION (3) REMOVE THE STOPPER (4) TRANSFER TO STOPPER BODY HOLD UNIT (5) LOWER THE SAMPLE CONTAINER AND TEMPORARILY KEEP THE STOPPER (C) FLOW OF STOPPERING (1) GRIP THE SAMPLE CONTAINER THAT HAS ARRIVED (2) LIFT THE SAMPLE CONTAINER TO STOPPERING POSITION AND TRANSFER THE STOPPER (3) MOUNT THE STOPPER (4) DETERMINE WHETHER STOPPERING IS COMPLETE (5) LOWER THE SAMPLE CONTAINER FROM STOPPERING POSITION AND RELEASE THE CONTAINER (1) ALLOCATE TO STOPPER BODY HOLD
UNIT (NO. 2)

(2) ROTATIONALLY MOVE TO
STOPPER BODY LOADING POSITION (3) TRANSFER THE STOPPER BODY 5
TO STOPPER BODY HOLD UNIT (4) CAUSE THE STOPPER BODY 5 TO STAND BY, AND HOLD THE STOPPER BODY 5

(5) MOVE THE STOPPER BODY 5 TO
STOPPER BODY UNLOADING POSITION
UPON REQUEST FOR UNLOADING THE
STOPPER BODY 5

(6) UNLOAD THE STOPPER
BODY 5

(7) CLEAN THE STOPPER BODY HOLD
UNIT (NO. 2)

(8) STAND BY

AUTOMATIC ANALYSIS SYSTEM WITH REMOVAL, TRACKING, AND MOUNTING OF STOPPER BODIES

TECHNICAL FIELD

The present invention relates to automatic analysis systems that analyze blood, urine, and other biological samples, and more particularly, to an automatic analysis system equipped with a destoppering/stoppering unit to remove a stopper body from/mount it on a container that accommodates such a sample.

BACKGROUND ART

Automatic analysis systems each include an automatic analyzer(s) to assay physical properties of such a biological sample as of blood or urine, or of a liquid mixture of the biological sample and a reagent(s), and thus to analyze the sample or the liquid mixture. These systems also include processing units to execute various steps such as destoppering a container that contains the sample, dispensing the sample, stoppering the container, stirring the sample, and analyzing the sample.

During the destoppering of containers in such an automatic analysis system, the plurality of destoppering/stoppering means described in Patent Documents 1 to 6, for example, are available as conventional techniques relating to a destoppering/stoppering unit that removes a stopper body from/mounts it on a sample container or a reagent container. Hereinafter, these operations are referred to as the destoppering/stoppering steps or processes.

The destoppering/stoppering means described in Patent Document 1 is of the following type. A test tube with a stopper body previously mounted thereupon is carried to a stopper cutoff position and after the stopper is clamped from both sides at the stopper cutoff position by a chuck, the chuck unit moves upward to remove the stopper from the test tube. Next after a reagent and/or the like is mixed into a sample contained in the test tube, the chuck unit moves downward to mount the stopper on the test tube.

In Patent Document 2, an automatic analyzer equipped with means to destopper/stopper a reagent container is provided, in which scheme, reliable destoppering/stoppering is possible when the stopper is one integrated with the container.

The stoppering device described in Patent Document 3 is such that the device is fitted with a positioning device for conveying a test tube and with stopper supply means for supplying a plurality of stoppers, one at a time, and such that the device mounts a stopper on the test tube by holding down the stopper from an upper surface using a chuck unit placed above the stoppering position. The conventional stoppering device in Patent Document 3 enables efficiently continuous mounting of stoppers on test tubes and is useable even in a confined place because of requiring no horizontal movement of paired chucks.

The stoppering device described in Patent Document 4 is such that the device can stopper an upper opening in the container reliably with mechanisms relatively simplified as a whole. In the conventional stoppering device according to Patent Document 4, successive stoppering steps from carrying the stopper to inserting it are distributed to the plurality of mechanisms, to enable streamlined stoppering and to render simple and reliable stoppering achievable by combining different insertion schemes different from each other.

In Patent Documents 5, 6, on the other hand, different kinds of means are provided that enable destoppering, even if test tubes of diverse sizes are mixedly used.

In Patent Document 5, test tube stopper removal means is provided that can remove stoppers rapidly and accurately even in a case that the mounted test tubes are of diverse sizes and the mounted stoppers vary in kind (push-fit rubber stoppers or cork stoppers and screwdown-type stoppers).

In Patent Document 6, a sample preprocessing system is provided that includes a destoppering unit capable of removing stoppers even in a case that sample containers of different heights (or of different stopper shapes and/or different stopper diameters) are mixedly present on one sample rack.

PRIOR ART LITERATURE

Patent Documents

Patent Document 1: JP-3-186354-A
Patent Document 2: Japanese Patent No. 2955613
Patent Document 3: JP-7-31890-A
Patent Document 4: JP-2003-98179-A
Patent Document 5: JP-2005-271991-A
Patent Document 6: JP-2009-36511-A

SUMMARY OF THE INVENTION

Problems to be Solved by the Invention

In conventional destoppering/stoppering mechanisms, it has been common that the removal and mounting of a stopper on a container containing a sample and a reagent in hermetically enclosed condition are done by separate mechanisms. In addition, the stopper body that has been removed from the container has been discarded and a new stopper body previously fitted on the sample container, for closing up the container, has been mounted thereupon.

As described in Patent Document 1, processing capabilities of the destoppering and stoppering mechanisms based on returning the stopper that was removed from the sample container to the same sample container have been determined by a time required for execution of one cycle from the removal of the stopper to the mounting thereof. That is to say, if the time required for the execution of the cycle from the removal of the stopper to the mounting thereof was 10 seconds, the destoppering/stoppering means has had a throughput of 3,600 seconds/10 seconds, equivalent to 360 stoppers/hour.

Under the situation that a processing rate of 1,000 tests/hour is becoming a standard in middle-scale models of automatic analyzers, the processing capability of 360 stoppers/hour has been liable only to reduce total system throughput.

An object of the present invention is to provide an automatic analysis system equipped with a stopper body removing/mounting mechanism adapted to reliably remove a stopper body from and mount it on a sample container without reducing total system throughput.

Means for Solving the Problem

The present invention has the following configuration to attain the above object.

An automatic analysis system equipped with a mechanism to transport a sample container having a stopper body, the system further including: a sample dispensing mechanism that dispenses a predetermined amount of sample accommodated in the sample container; a stopper body removing/mounting mechanism that removes the stopper body from the sample container; a control unit that stores therein association between the sample container and the stopper body of the sample container; the stopper body removing/mounting mechanism that in accordance with the association stored into the control unit, mounts the stopper body back on the sample container into which the sample dispensing mechanism has dispensed the sample; and a stopper body transport mechanism that transports the sample that the stopper body removing/mounting mechanism has removed at a stopper removing position to the stopper mounting mechanism.

The automatic analysis system means an analysis system including a preprocessing apparatus which conducts centrifuging, child-sample dispensing, destoppering, stoppering, bar-code labeling, and various other preprocessing steps for analyzing samples in automatic analyzers.

Although the system may include automatic analyzers, it suffices if the system is equipped with at least destoppering, stoppering, and dispensing mechanisms and a mechanism that transports the sample therebetween.

The stopper body is formed from rubber, plastic, or the like, to prevent leaking of the sample accommodated in the sample container, and may be of a screwdown type or may be of a type that is only press-fit.

The sample container is a container charged with the sample to be analyzed, and it suffices if the container can be transferred, whether it is mounted on a rack or a holder.

The stopper body removing/mounting mechanism can be any one, only if it can conduct the destoppering step for removal of the stopper body and the stoppering step for mounting of the stopper body. Alternatively this mechanism can be one capable of holding and managing the stopper body from the destoppering step to the stoppering step.

In addition, the stopper body transport mechanism in the automatic analysis system can hold a plurality of stopper bodies that the stopper body removing/mounting mechanism has removed.

Furthermore, the stopper body transport mechanism in the automatic analysis system includes a stopper body hold mechanism configured to hold the plurality of stopper bodies that the stopper body removing/mounting mechanism has removed at the stopper removing position, and transport any of the stopper bodies to a stopper mounting position. The stopper body hold mechanism can be any one configured to hold the plurality of stopper bodies that the stopper body removing/mounting mechanism has removed at the stopper removing position, and transport any of the stopper bodies to a stopper mounting position. These mechanism are commonly of a shape resembling either a belt conveyor, a shape resembling a turntable, a type that uses a robot arm to transport the stopper body in the air, or other types or shapes.

Effects of the Invention

The present invention enables reliable destoppering and stoppering of a sample container on a container transfer line of the automatic analysis system. The system can therefore dispense a sample stably and provide highly reliable analytical and measurement results.

MODE FOR CARRYING OUT THE INVENTION

Hereunder, a first embodiment of the present invention will be described referring to the accompanying drawings.

Figure 1:
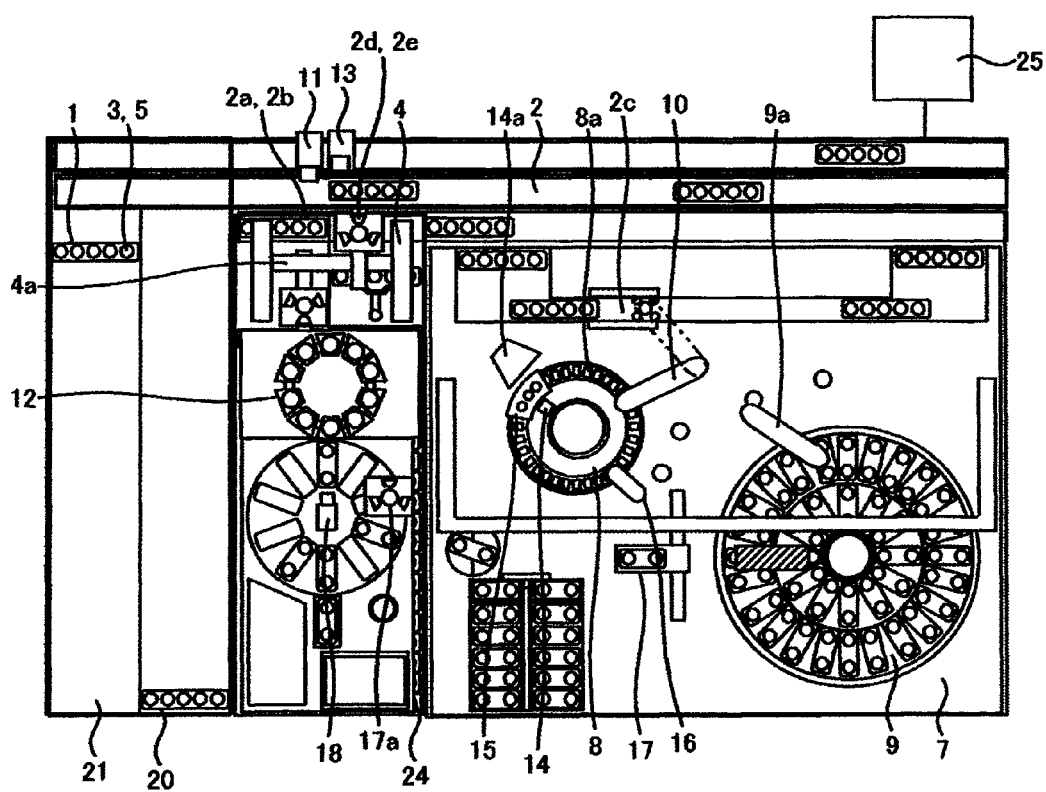
FIG. 1, which relates to a first embodiment of the present embodiment, is a schematic diagram showing an overall configuration of an automatic analysis system equipped with a mechanism for removing and mounting a stopper body for a sample container.

FIG. 1 is a schematic diagram showing an overall configuration of an automatic analysis system according to the present embodiment. The automatic analysis system is equipped with the following: a transport mechanism 2 that transfers a rack 1, on which sample containers 3 each containing a biological sample of, for example blood or urine in a hermetically enclosed condition, are mounted; a stopper body removing/mounting mechanism 4 that conducts a destoppering process to remove a stopper body 5 from one of the sample containers 3 which have been transferred by the transport mechanism 2, and a stoppering process to mount the stopper body 5 once again; and a stopper body hold mechanism 12 that holds and transports the stopper body.

Figure 2:
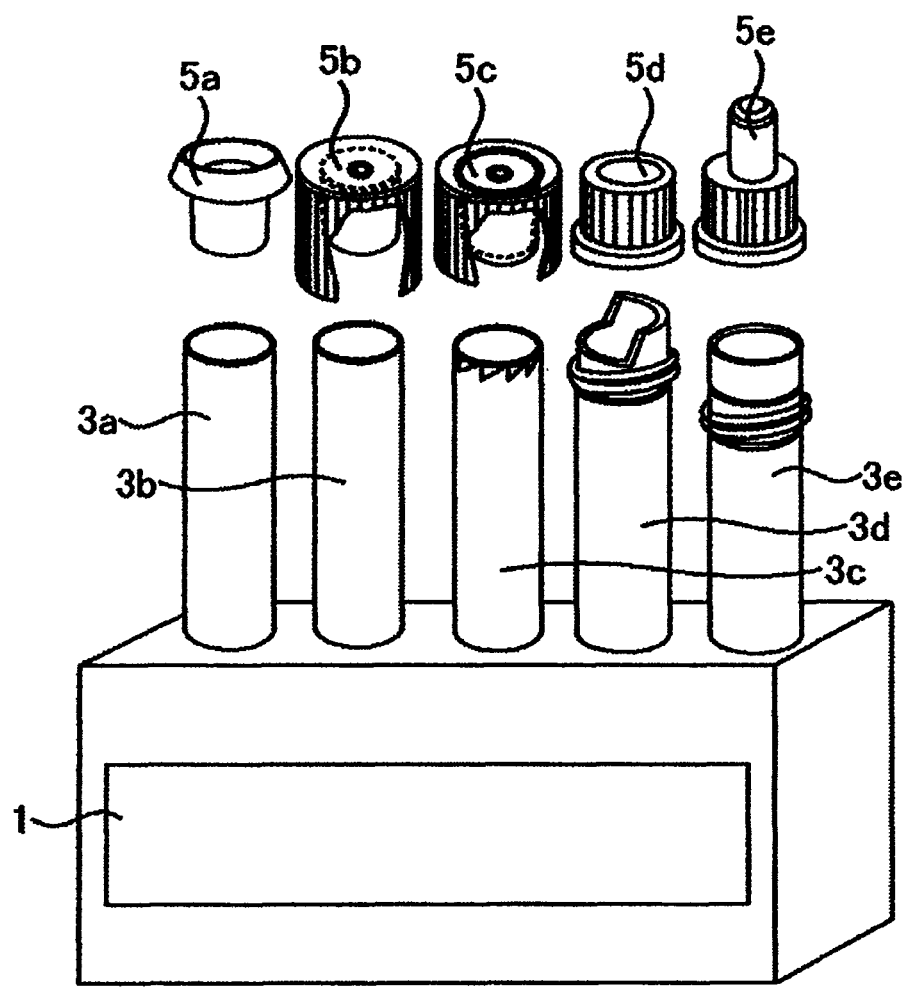
FIG. 2, which relates to the embodiments, shows one of a plurality of sample containers mounted on a rack.

FIG. 2 is a schematic view showing one of a plurality of sample containers 3 and a plurality of stopper bodies 5 mounted on the rack 1.

Figure 3A:
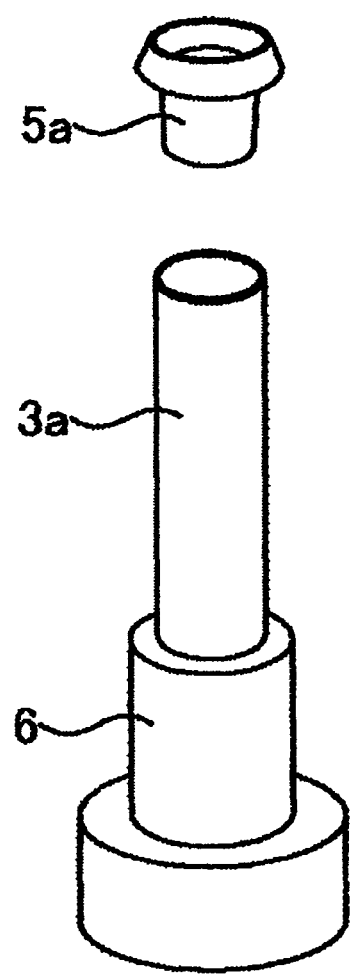
FIG. 3A, which relates to the embodiments, shows one of a plurality of sample containers mounted on a holder.
Figure 3B:
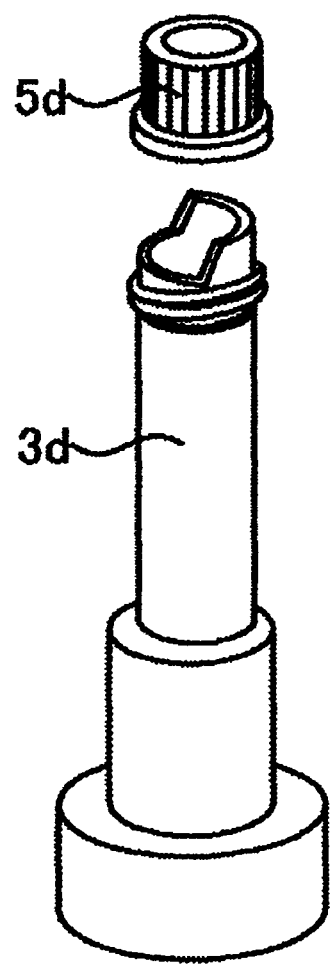
FIG. 3B, which relates to the embodiments, shows one of a plurality of sample containers mounted on a holder.
Figure 3C:
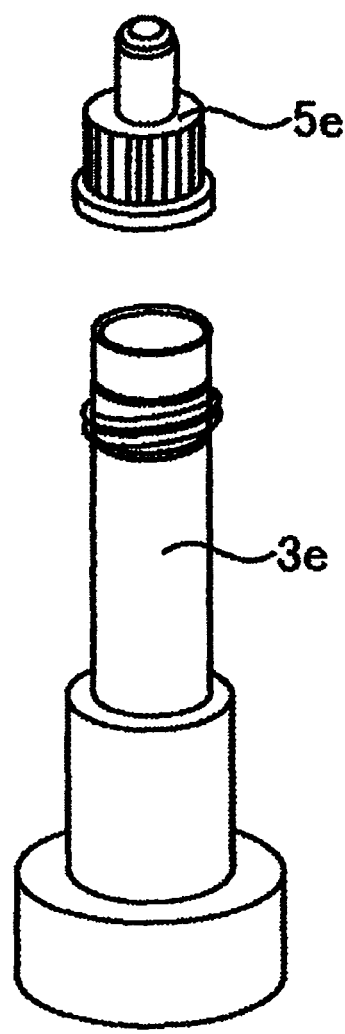
FIG. 3C, which relates to the embodiments, shows one of a plurality of sample containers mounted on a holder.
Figure 4A:
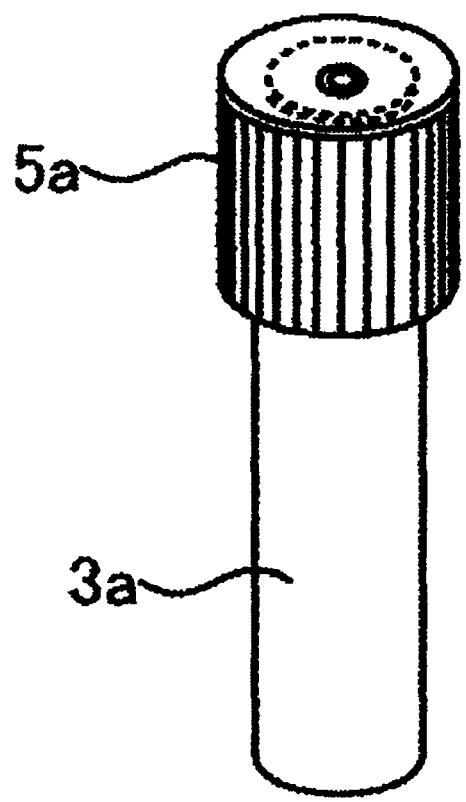
FIG. 4A, which relates to the embodiments, is a schematic view showing an identification process relating to a sample container and a stopper body.
Figure 4B:
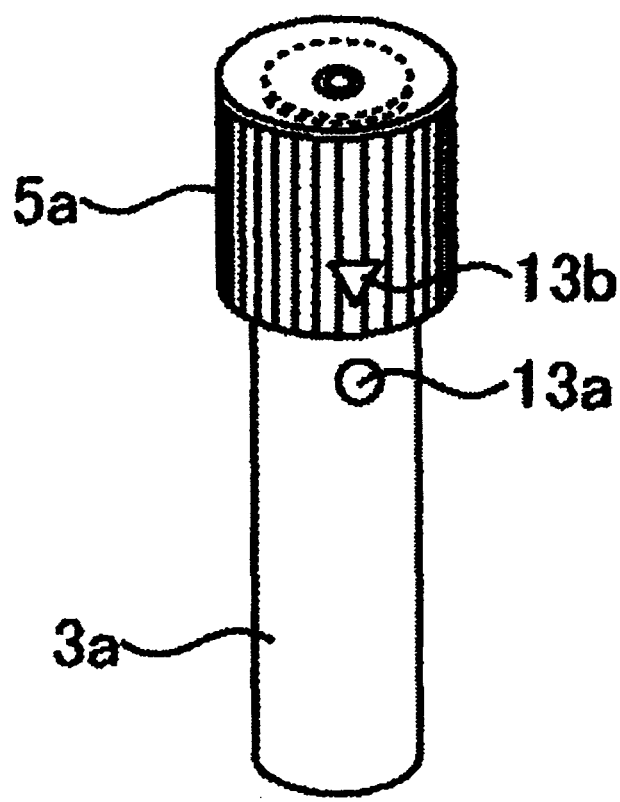
FIG. 4B, which relates to the embodiments, is the schematic view showing an identification process relating to a sample container and a stopper body.
Figure 4C:
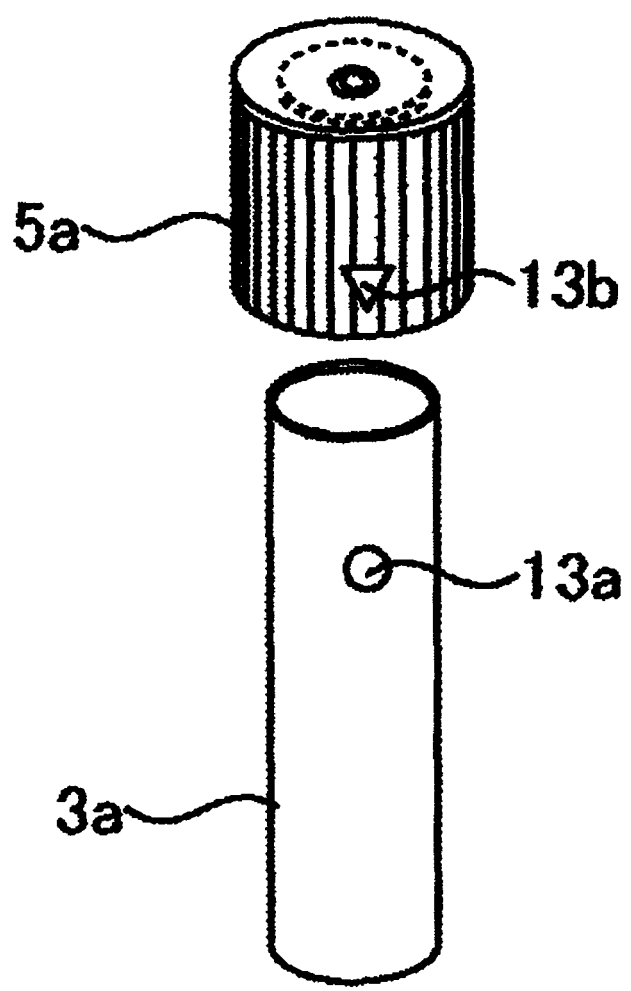
FIG. 4C, which relates to the embodiments, is the schematic view showing an identification process relating to a sample container and a stopper body.
Figure 4D:
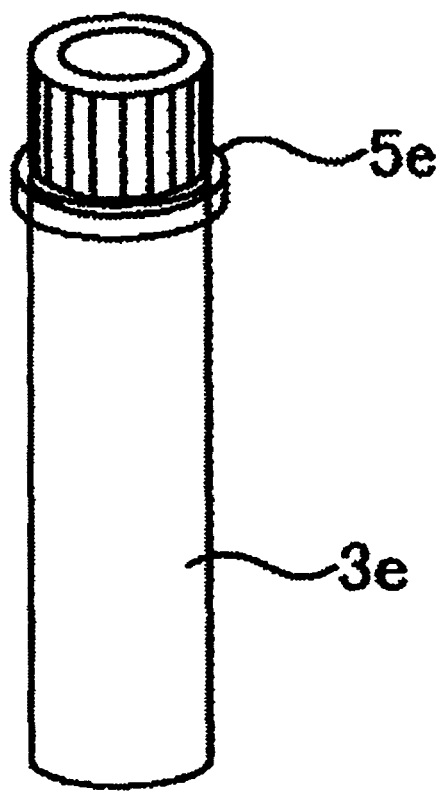
FIG. 4D, which relates to the embodiments, is the schematic view showing an identification process relating to a sample container and a stopper body.
Figure 4E:
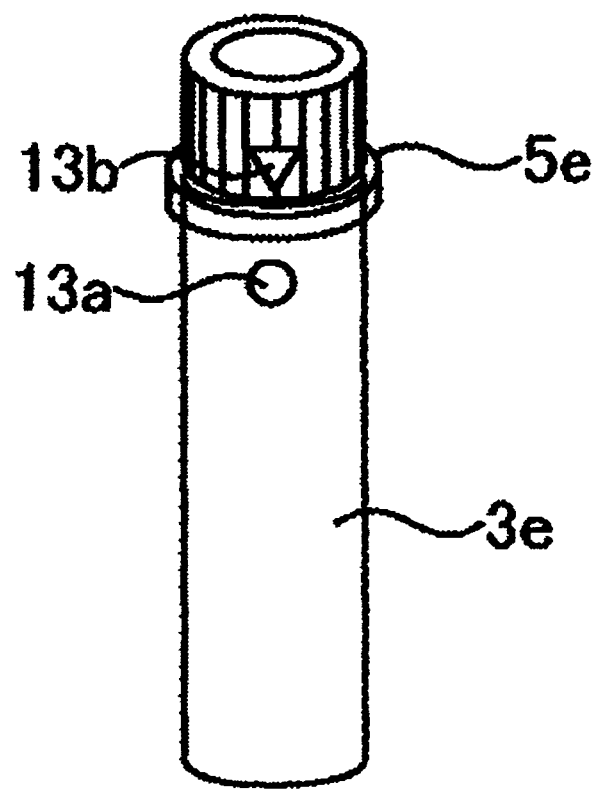
FIG. 4E, which relates to the embodiments, is the schematic view showing an identification process relating to a sample container and a stopper body.
Figure 4F:
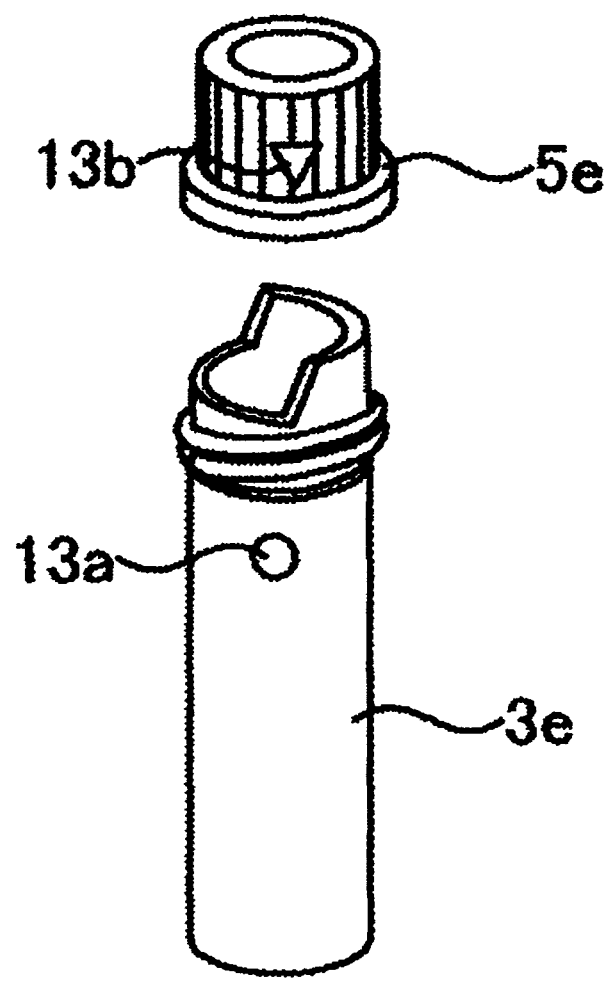
FIG. 4F, which relates to the embodiments, is the schematic view showing an identification process relating to a sample container and a stopper body.

FIGS. 3A to 3C are schematic views each showing one of a plurality of sample containers 3 and a plurality of stopper bodies 5 mounted on a holder 6.

Each sample container 3 has an opening for accommodating or removing the biological sample, and is blocked up with a stopper body 5 to suppress unwanted events such as entry of foreign matter, evaporation of internal contents, or spilling of the biological sample due to a turnover of the container 3.

While the stopper body 5 has a cylindrical shape of a diameter larger than that of the opening in the sample container 3 and is formed from rubber, plastic, or equivalent, the stopper body 5 can be of any shape and material, provided that it prevents the accommodated sample from spilling. The stopper bodies 5a to 5c are mounted by press-fitting in the openings of the sample containers 3a to 3c, and the stopper bodies 5d and 5e are threadably mounted in the openings of the sample containers 3d and 3e.

The stopper body 5a-5c can be removed from the opening of the sample container 3a-3c by pulling out the stopper body after shaking it or rotating it in a circumferential direction. The stopper body 5d, 5e can be removed by pulling it out after rotating it along a threaded portion of a mating part provided in a circumferential direction.

Although not shown, identification numbers 1a and 6a, 6d, or 6e are preassigned to predetermined positions on the rack 1 and the holder 6, respectively, and the identification numbers of the rack 1 and the holder 6 can be determined by image processing. Each sample container 3a-3e is also preassigned an identification number, such as a bar code, that is not shown in the figure, and the identification number of the sample container 3a-3e can be determined by image processing.

Referring to FIG. 1, a plurality of reaction vessels 8a are arranged in a regular way on a circumference of a unidirectionally turnable reaction disk 8 placed on an housing 7 of the automatic analysis system. In addition, a reagent disk 9 is placed on the housing 7 so as to be rotatable in two directions, and is constructed so that the reagent disk 9 rotates in the direction that a necessary reagent takes up a position proximate to a reagent probe 9a. Each of the reagent probe 9 is connected to sampling pumps not shown. The reagent disk 9 is also constructed so that reagent containers 9b that contain a plurality of reagents of different kinds to be used for analysis can be rested on the entire circumference of the reagent disk 9. The transport mechanism 2 that transfers racks 1 each having sample containers 3 mounted thereupon is installed near the reaction disk 8. Between the reaction vessels 8a and the transport mechanism 2 is placed a rotatable and vertically movable sample probe 10, which is connected to sampling pumps not shown in the figure. A light source 14, a detection optical device 14a, a container washing mechanism 15, and a stirrer 16 are arranged around the reaction disk 8. The container washing mechanism 15 is connected to a washing pump not shown in the figure. Washing ports are placed in respective operating zones of the sample probe 10, the reagent probe 9a, and the stirrer 16. The sampling pumps, reagent pumps, and the washing pump, none of which is shown, are each connected to a control computer 25. Also connected to the control computer 25 respectively are, the detection optical device 14a, the reaction vessels 8a, the reagent disk 9, the reagent probe 9a, the sample probe 10, a reagent container hold mechanism 17, a reagent container destoppering mechanism 17a, and a reagent container information reading mechanism 18.

A sample information reading mechanism 11 for reading information about the sample enclosed in the sample container 3, and a stopper body identification mechanism 13 for identifying the stopper body 5 are arranged on a transfer line of the sample container 3. Near the sample information reading mechanism 11 located at an upstream side of a position 2c at which the sample probe 10 collects the sample, the stopper body removing/mounting mechanism 4 and the stopper body hold mechanism 12 are arranged. The stopper body removing/mounting mechanism 4 conducts the destoppering process to remove the stopper body 5 from the sample container 3 and the stoppering process to mount the stopper body 5 once again. While, the stopper body hold mechanism 12 causes the removed stopper body 5 to temporarily stand by and transports and keeps the stopper body 5.

The stopper body removing/mounting mechanism 4 includes a transport arm 4a that enables a stopper body chuck mechanism 4b to be relocated in three axial directions, the stopper body chuck mechanism 4b that enables the stopper body 5 to be gripped and removed/mounted, and a clamp 4c that grips the sample container 3 and relocates it vertically. Depending upon throughput of the automatic analysis system, the stopper body chuck mechanism 4b and the clamp 4c exist in at least one place, and these stopper body chuck mechanisms 4b and clamps 4c are connected to the transport arm 4a. The sample information reading mechanism 11, the stopper body identification mechanism 13, the stopper body removing/mounting mechanism 4, and the stopper body hold mechanism 12 are connected to the control computer respectively. Depending upon the kind of stopper body, the stopper body removing/mounting mechanism 4 can switch its operation to the destoppering process for removing the stopper body of the sample container, or to the stoppering process for mounting the stopper body on the sample container.

An analytical sequence using the system is described below.

Before the analysis is started, maintenance is first conducted. The maintenance includes operations such as checking the detection optical device 14*a*, washing the reaction vessel 8*a*, and washing the sample probe 10 and other probes.

A sample to be tested, such as blood or urine, is enclosed in a sample container 3 by an operator and after this sample container has been blocked with a stopper body 5, the sample container 3 is mounted on a container transfer rack 1 or holder 6 and then loaded into the automatic analysis system from a sample loading unit 21. The transport mechanism 2 transfers the rack 1 or the holder 6. After the transport mechanism 2 has transferred the rack 1 to a sample information reading position 2*a*, the sample information reading mechanism 11 reads the sample information.

First, a geometry (diameter, height and kind) of the sample container 3 are identified. Along with this, the stopper body identification mechanism 13 detects the stopper body 5 and identifies a shape thereof, that is, determines whether the stopper body 5 is of the press-fit type (5*a*-5*c*) or the screwdown type (5*d*, 5*e*). A receiving date and receiving number of the sample, patient attributes, a ward identification, and other information relating to the sample container 3 are also stored into the control computer 25.

Examples of identifying stopper bodies 5 are shown in FIGS. 4A to 4F.

An identification process for associating one sample container 3 with one stopper body 5 is conducted by printing and machining. The identification process assigns a lot number, a bar-code number, and other identification numbers to the stopper body 5. Codes 13*a* and 13*b* for positioning the stopper body 5 with respect to the sample container 3 are also added. The identification process for the stopper body 5 may be conducted upon any position, whether it be on an outer surface or upper end face of the stopper body 5, only if the stopper body 5 can be identified. In addition, the above identification numbers and positioning codes may be assigned before the sample container 3 and the stopper body 5 are formed by molding, for example.

The execution of the identification process associates the sample container 3 and the stopper body 5 with each other and thus enables direct management of the stopper body 5. In addition to management of the rack 1 and the holder 6 by respective identification numbers, the sample container 3 and the stopper body 5 are associated and managed by the respective identification numbers.

When it is desired that the automatic analysis system cause the sample in the sample container 3 to be rapidly analyzed, there may arise a case in which, while the stopper body 5 is removed, overtaking is caused to a particular sample container 3 and thereby the order of sampling (dispensing) and stoppering is reversed.

If the sample container 3 is not associated with the stopper body 5, first-in first-out processing becomes necessary in each of the destoppering, sampling (dispensing), and stoppering processes. In the present embodiment, since the sample container 3 is associated with the stopper body 5, the stopper body 5 that has been removed from the sample container 3 can be remounted without fail, even if the order of each processes has changed. Rapid processing of the sample container 3 can therefore be executed. Even if a failure in the mechanism of a part of the automatic analysis system occurs and measurement is temporarily suspended, there is no problem since the association between the sample container 3 and the stopper body 5 is already established.

Figure 5A:
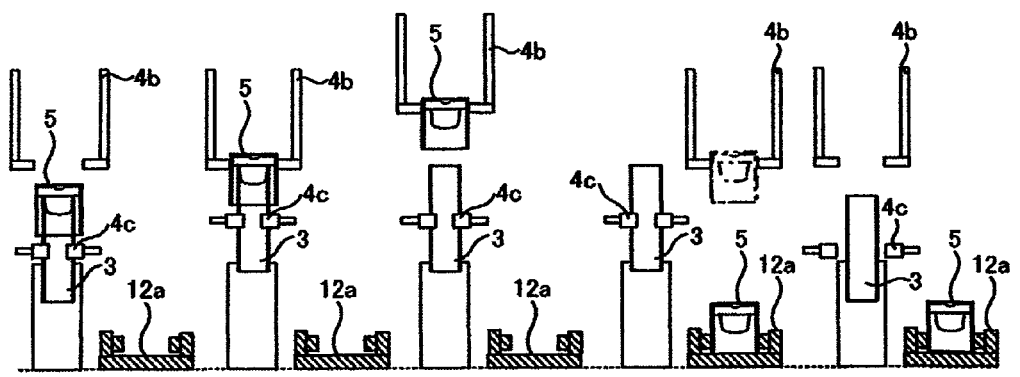
FIG. 5A, which relates to the embodiments, is a sequence pattern diagram of operation from destoppering a sample container to stoppering the container.

Next, the transport mechanism 2 transfers the sample container 3 to a position under a destoppering position 2*b*. The sample information reading position 2*a* and the destoppering position 2*b* can be the same. A flow of destoppering is shown in FIG. 5A. As shown in FIGS. 5A-(1), (2), the sample container 3 that has been transferred to the position under the destoppering position 2*b* is lifted to the destoppering position while being gripped by the clamp 4*c* of the stopper body removing/mounting mechanism 4. The stopper body chuck mechanism 4*b* removes the stopper body 5 from the sample container 3, as shown in FIG. 5A-(3). At this time, the stopper body removing/mounting mechanism 4 conducts the destoppering process relevant to the sample container 3 and stopper body 5 that have been identified and determined by the sample information reading mechanism 11 and the stopper body identification mechanism 13, respectively.

The stopper body removing/mounting mechanism 4 and the stopper body identification mechanism 13 determine the stopper body 5 to have been removed from the sample container 3, this determination being conducted via sensors 4*e* and 13*a* not shown. If the stopper body 5 is not yet removed from the sample container 3, retrial operation is executed to repeat the destoppering process once again. As shown in FIGS. 5A-(4), (5), the removed stopper body 5 is transferred to a stopper body hold unit 12*a* of the stopper body hold mechanism 12 by the transport arm 4, and then the stopper body 5 is temporarily kept in the stopper body hold unit 12*a*.

The above destoppering process is repeated for all sample containers 3 present on the rack 1. After the destoppering process has been repeated any number of times set by the operator, if there is a sample container 3 determined not to be fully destoppered, appropriate information is output from the control computer 25 and at the same time the particular sample container 3 is returned to a retest sample storage unit 24 and undergoes processing by the operator. The operator confirms external states of the sample container 3 and the stopper body 5. If no abnormality is detected, the sample container 3 can be reloaded from the sample loading unit 21.

Next, the transport mechanism 2 carries the sample container 3 to the sampling position 2*c*. The sample information reading position 2*a*, the destoppering position 2*b*, and the sampling position 2*c* may be the same.

Figure 5B:
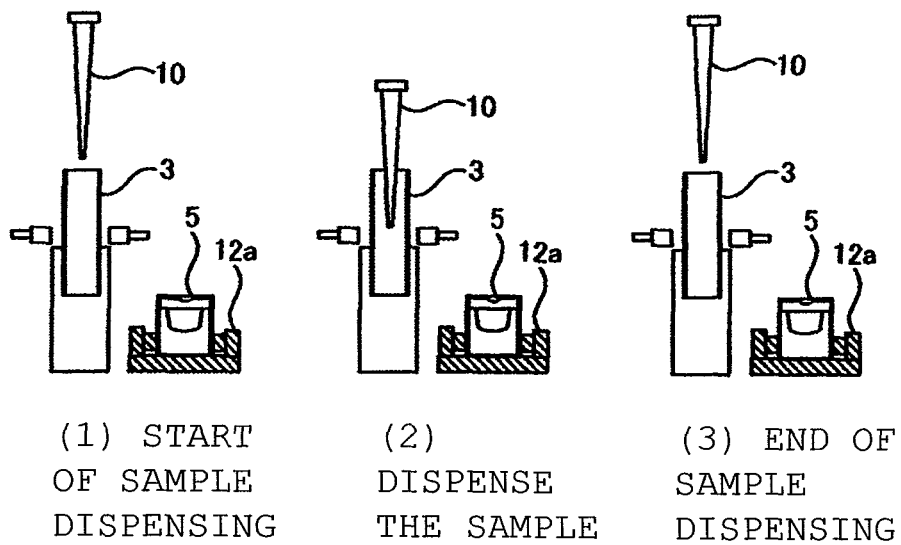
FIG. 5B, which relates to the embodiments, is the sequence pattern diagram of the operation from destoppering the sample container to stoppering the container.

A flow of dispensing is shown in FIG. 5B. The sample probe 10 acquires the sample from the sample container 3 that has been transferred to the sampling position 2*c*. During this sampling operation, the stopper body hold unit 12*a* is holding the removed stopper body 5. The sample that has been collected by the sample probe 10 is dispensed in fixed quantities into the reaction vessels 8*a* arranged on the reaction disk 8, fixed quantities of reagent are dispensed from the reagent containers 9*b* on the reagent disk 9 by the reagent probe 9*a*, and the dispensed sample and reagent are stirred by the stirrer 16. After a fixed time of reaction, the detection optical device 14*a* measures absorbance, spectrum, and other factors of the mixture contained in each reaction vessel 8*a*, and measurement results are output to the control computer 25. The above sampling operation is repeated if there are even more requested measurement items. Sampling is repeated until the measurement items set for the sample enclosed in all the sample containers 3 present on the rack 1 have been executed.

Next, each sample container 3 from which sampling has been executed is transferred to a sample information reading position 2*d* by the transport mechanism 2. The sample information reading position 2*a*, the destoppering position 2*b*, the sampling position 2c, and the sample information reading position 2d can be the same. The sample information reading mechanism 11 and the control computer 25 identify the stopper body 5 corresponding to the sample container 3. The control computer 25 issues a request for unloading the identified stopper body 5 from the stopper body hold mechanism 12.

The sample container 3 is transferred to a stoppering position 2e by the transport mechanism 2. The sample information reading position 2a, the destoppering position 2b, the sampling position 2c, the sample information reading position 2d, and the stoppering position 2e can be the same. The stopper body 5 corresponding to the sample container 3 is unloaded from the stopper body hold mechanism 12 and stoppering the stopper body 5 is performed.

Figure 5C:
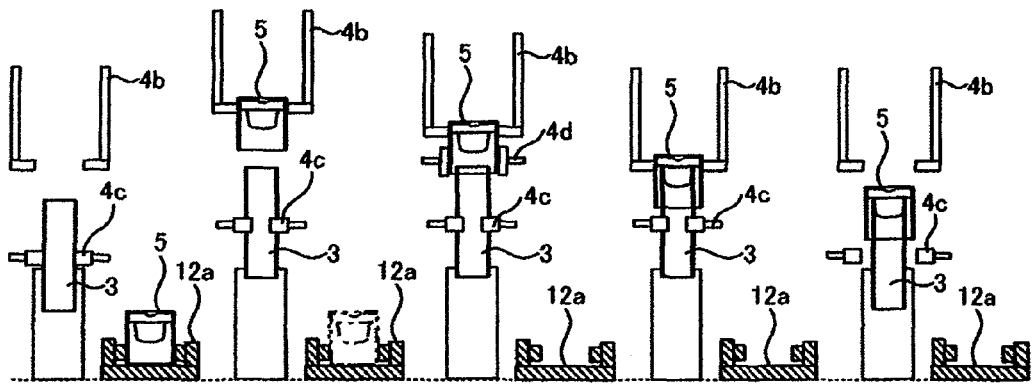
FIG. 5C, which relates to the embodiments, is the sequence pattern diagram of the operation from destoppering the sample container to stoppering the container.

A flow of stoppering is shown in FIG. 5C. The sample container 3 that has been transferred to the stoppering position 2e is gripped by the clamp 4c of the stopper body removing/mounting mechanism 4, as shown in FIG. 5C-(1). After this, as shown in FIG. 5C-(2), (3), (4), the sample container 3 is lifted and the stopper body 5 is transferred to an upper coaxial section of the sample container 3 by the transport arm 4a and then the stopper body 5 is mounted by the stoppering operation of the stopper body chuck mechanism 4b. At this time, the stopper body removing/mounting mechanism 4 conducts the stoppering process relevant to the sample container 3 and stopper body 5 identified and determined by the sample information reading mechanism 11 and the stopper body identification mechanism 13, respectively.

Figure 6A:
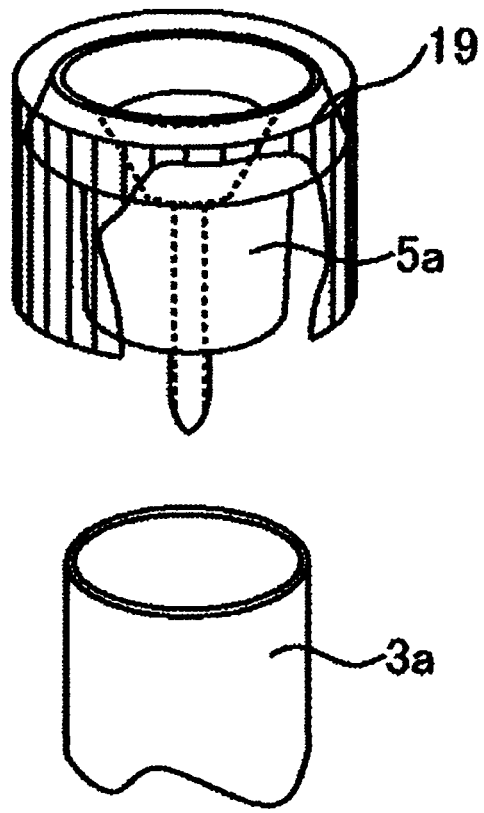
FIG. 6A, which relates to the embodiments, is a schematic view showing a mechanism for protecting the stopper body on the sample container.
Figure 6B:
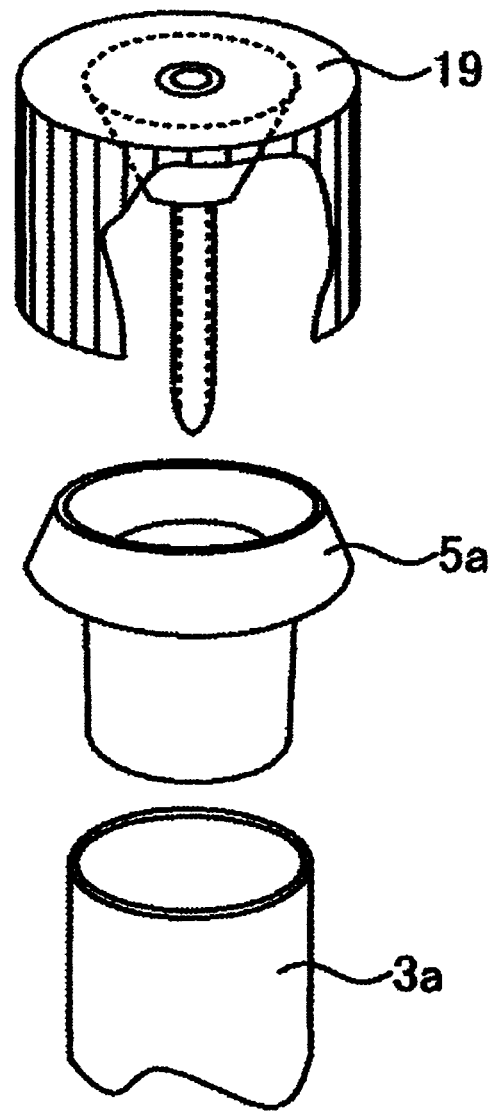
FIG. 6B, which relates to the embodiments, is the schematic view showing a mechanism for protecting the stopper body on the sample container.
Figure 6C:
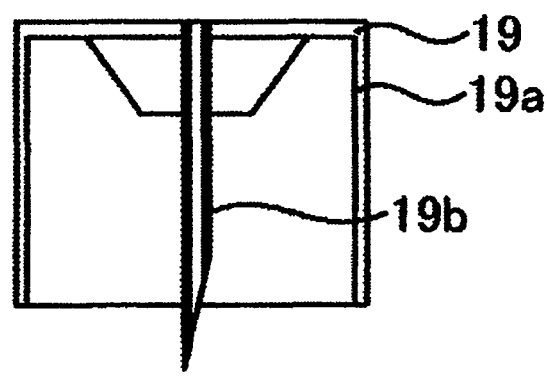
FIG. 6C, which relates to the embodiments, is the schematic view showing a mechanism for protecting the stopper body on the sample container.
Figure 6C:
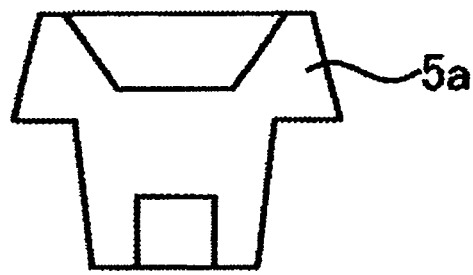
Figure 6C:
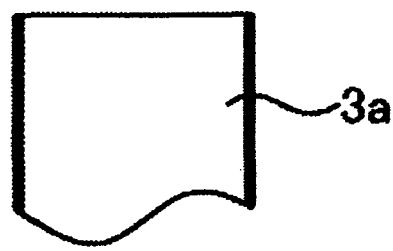

Schematic views of a stopper body protecting mechanism 19 having a stopper body 5a screwed down thereunto are shown in FIGS. 6A to 6C. The stopper body protecting mechanism 19 has a conical protrusion on a top panel inner side face of a cylindrical closure 19a formed from a metal or plastic, and includes a pierced portion 19b as well. Mounting the stopper body protecting mechanism 19 over the stopper body 5a enables the stopper body chuck mechanism 4b to grip the stopper body 5a via the stopper body protecting mechanism 19. The stopper body removing/mounting mechanism 4 can conduct the destoppering or stoppering process by using the stopper body protecting mechanism that matches the stopper body to be removed or mounted.

For example, if the stopper body 5a is such an elastic body as formed from rubber, a gripping force of the stopper body chuck mechanism 4b is likely to deform the stopper body 5a. Screwing down the stopper body protecting mechanism 19 onto the stopper body 5a leads to smooth destoppering or stoppering. In addition to the above, after the stopper body 5a has been mounted on the sample container 3, in cases that an internal temperature of the sample container 3 increases, a change in an internal pressure thereof is like to cause the stopper body 5 to come off. Screwing down the stopper body protecting mechanism 19 onto the stopper body 5 enables the internal pressure of the sample container 3 to be adjusted and hence the stopper body 5 to be removed or mounted smoothly. The stopper body identification mechanism 13 confirms a mounted state of the mounted stopper body 5.

Figure 7A:
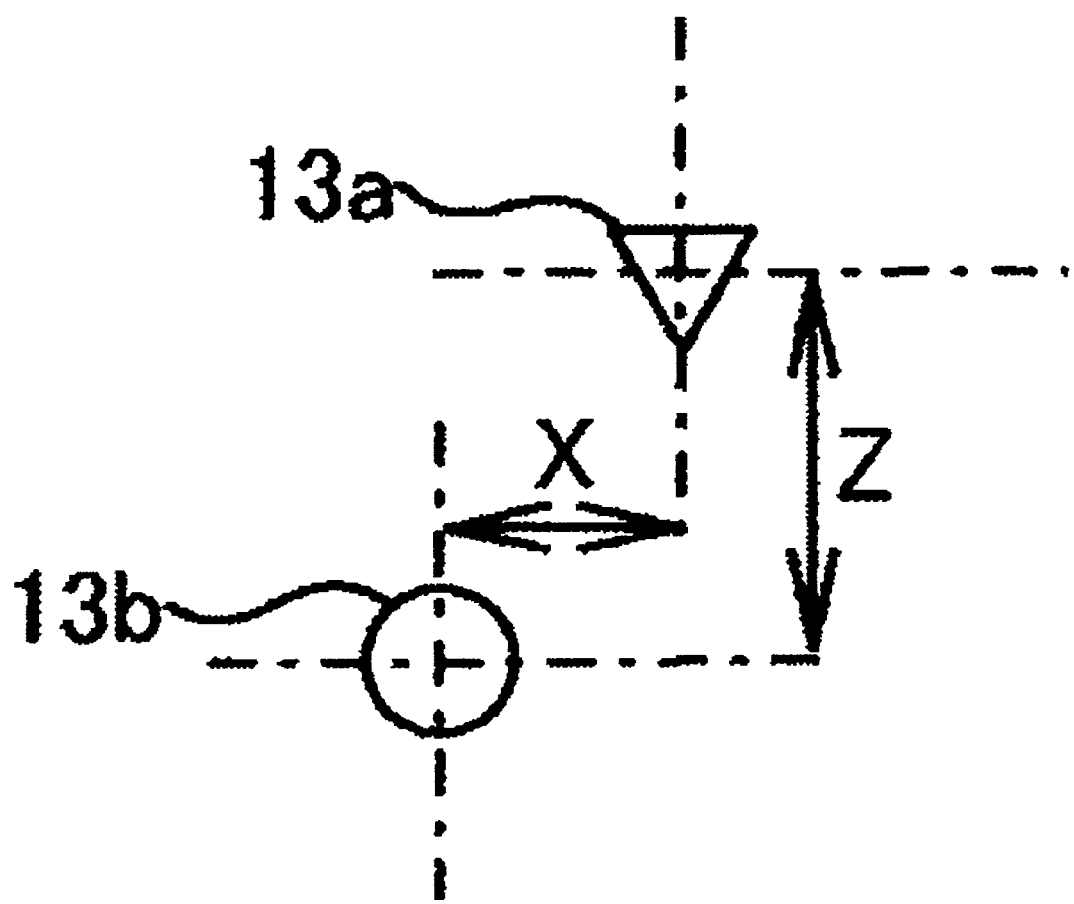
FIG. 7A, which relates to the embodiments, is a schematic diagram showing a manner of determining whether the stopper body has been mounted.
Figure 7B:
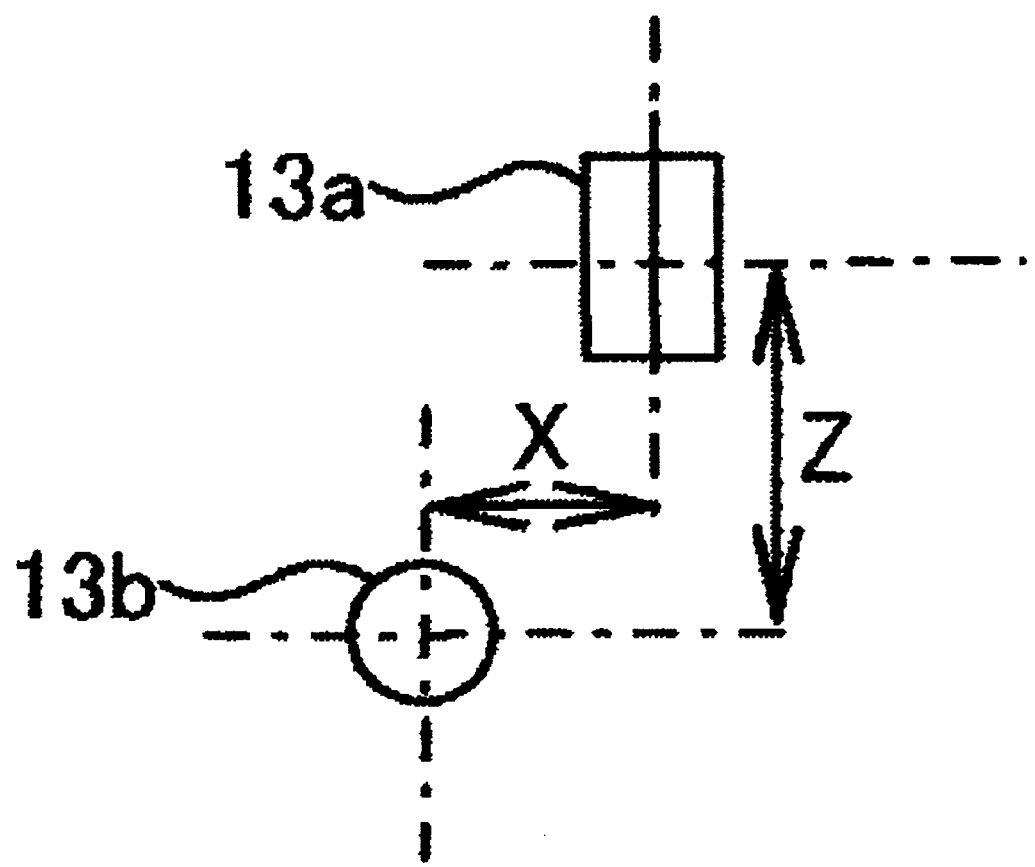
FIG. 7B, which relates to the embodiments, is the schematic diagram showing the manner of determining whether the stopper body has been mounted.
Figure 7C:
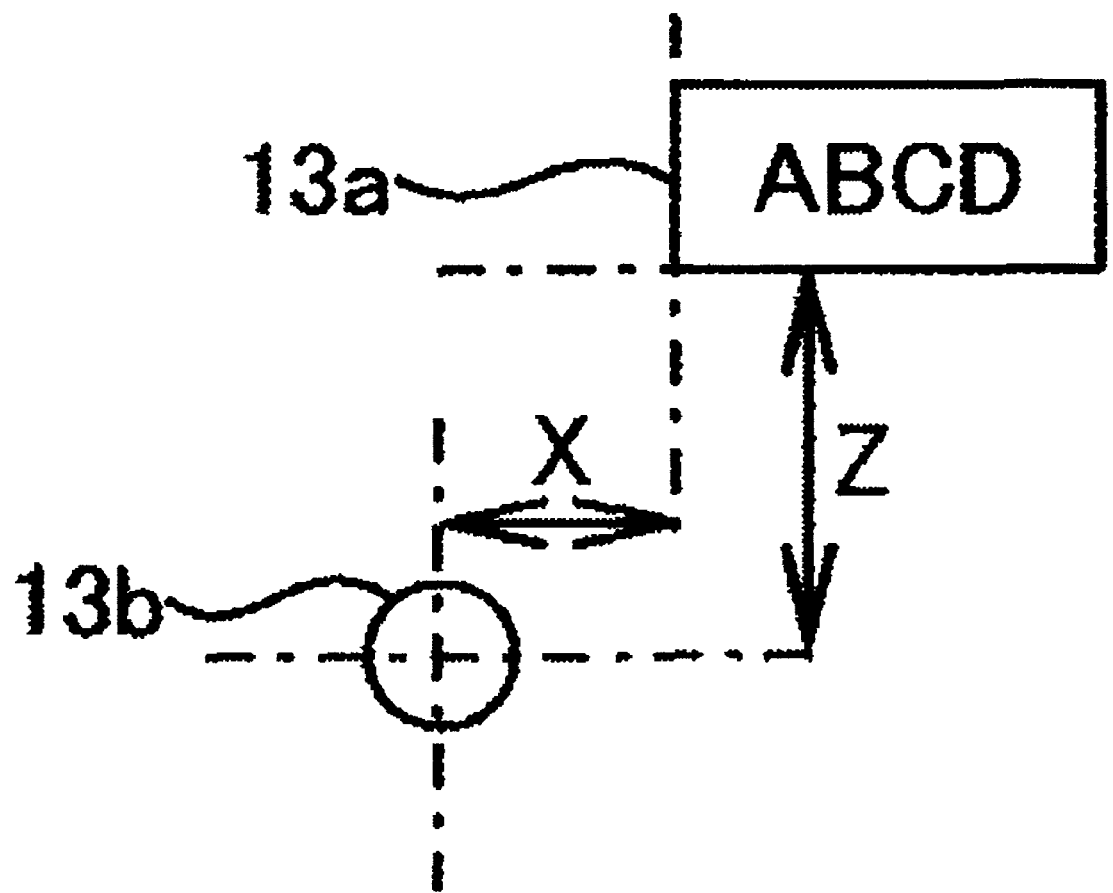
FIG. 7C, which relates to the embodiments, is the schematic diagram showing the manner of determining whether the stopper body has been mounted.
Figure 8A:
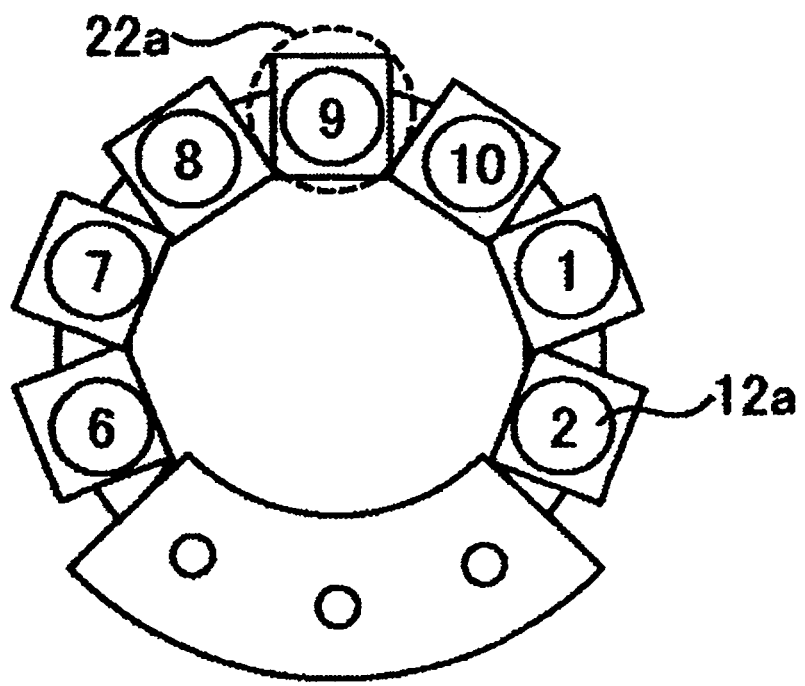
FIG. 8A, which relates to the embodiments, is a sequence pattern diagram of operation in a stopper body hold mechanism.
Figure 8B:
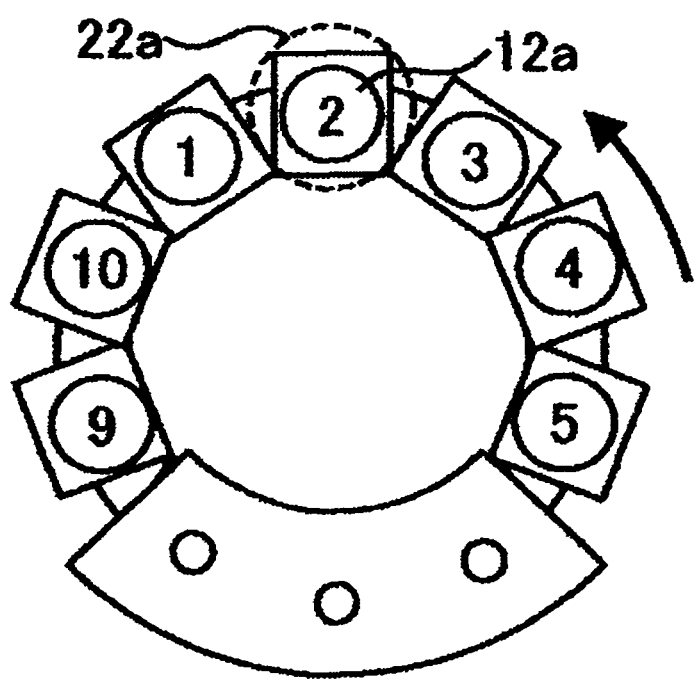
FIG. 8B, which relates to the embodiments, is the sequence pattern diagram of the operation in the stopper body hold mechanism.
Figure 8C:
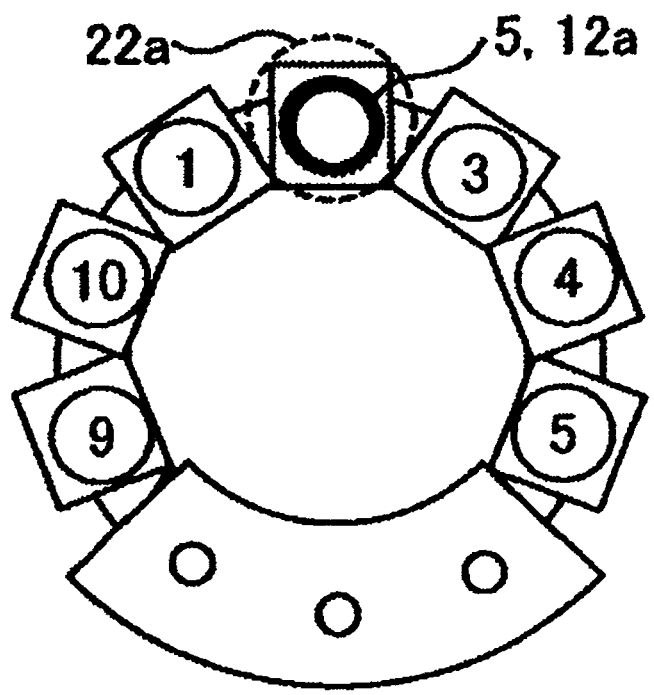
FIG. 8C, which relates to the embodiments, is the sequence pattern diagram of the operation in the stopper body hold mechanism.
Figure 8D:
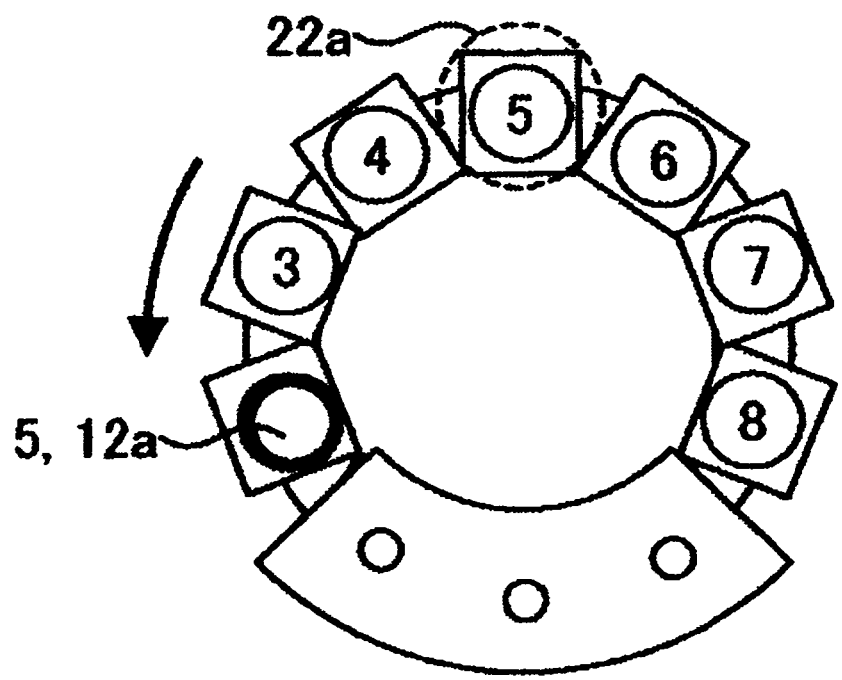
FIG. 8D, which relates to the embodiments, is the sequence pattern diagram of operation in a stopper body hold mechanism.
Figure 8E:
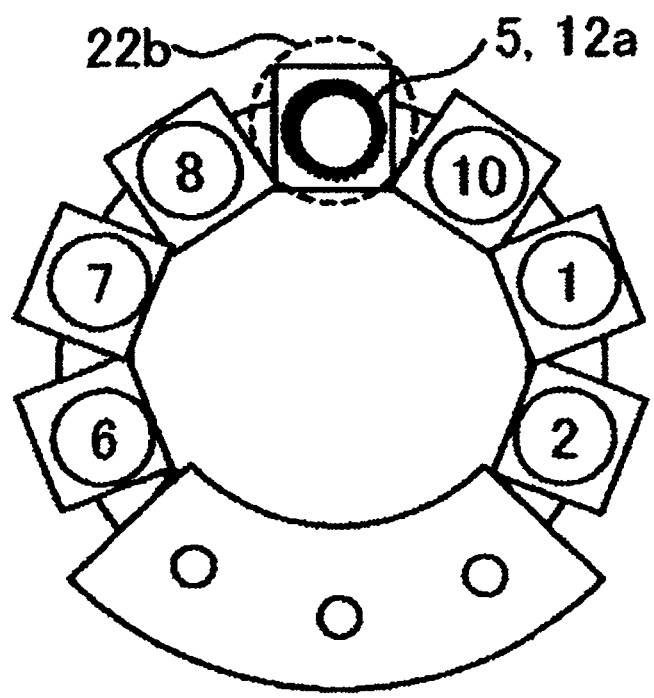
FIG. 8E, which relates to the embodiments, is the sequence pattern diagram of the operation in the stopper body hold mechanism.
Figure 8F:
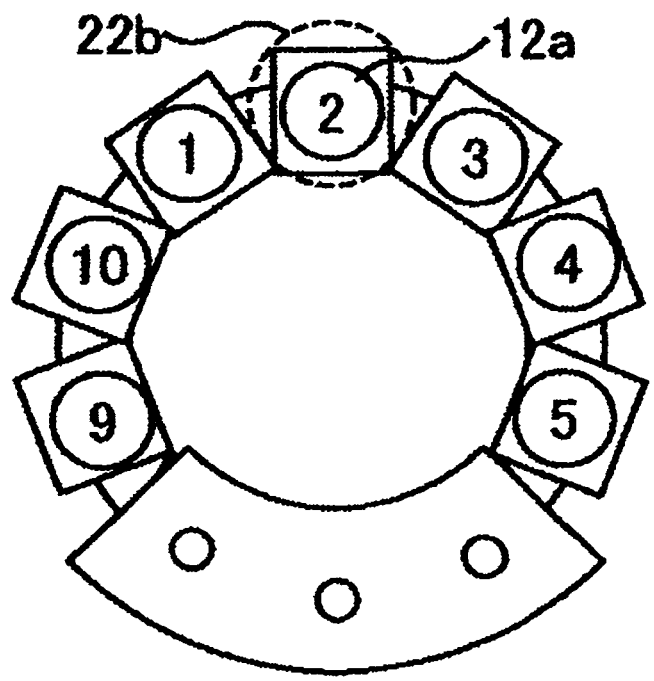
FIG. 8F, which relates to the embodiments, is the sequence pattern diagram of the operation in the stopper body hold mechanism.
Figure 8G:
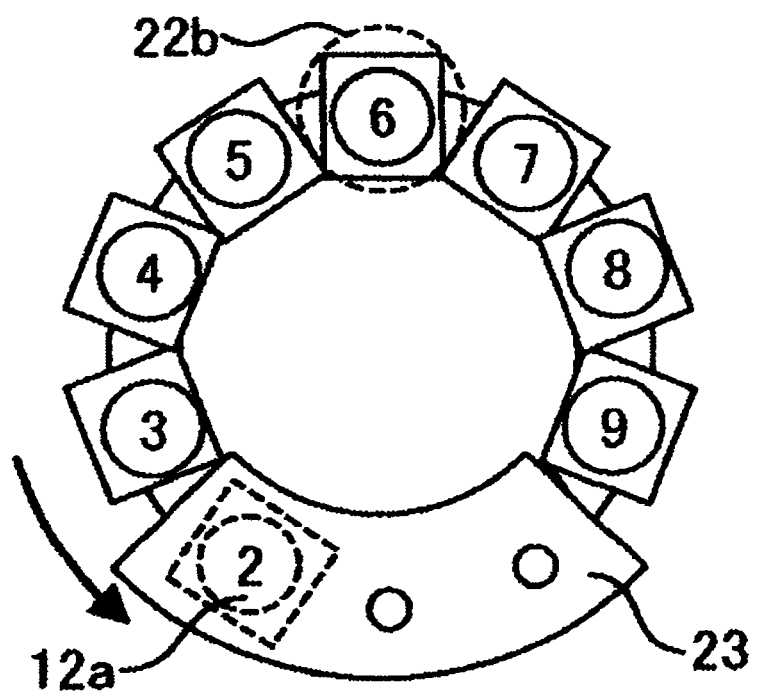
FIG. 8G, which relates to the embodiments, is the sequence pattern diagram of the operation in the stopper body hold mechanism.
Figure 8H:
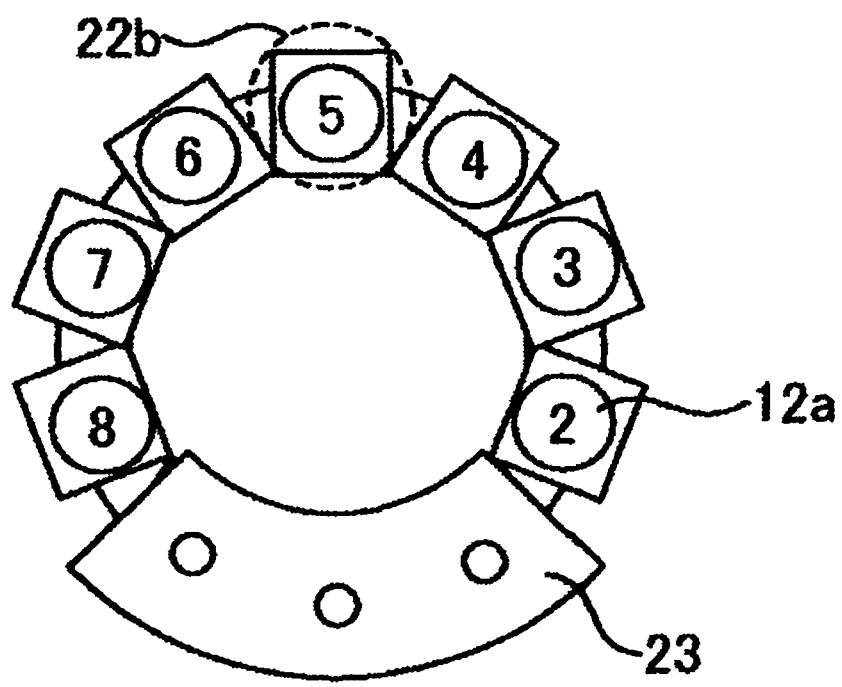
FIG. 8H, which relates to the embodiments, is the sequence pattern diagram of the operation in the stopper body hold mechanism.

A flow of the stoppering confirmation is shown in FIGS. 7A to 7C. Before destoppering is started, the stopper body identification mechanism 13 measures a fitting size (Z) and circumferential screwdown size (X) of the stopper body 5 as mounted on the sample container 3, the measurements being based on the positioning codes 13a, 13b of the previously identified stopper body 5. A difference between the measured data (Z, X) and a previously set threshold value is determined by the control computer 25, whereby whether or not the stoppering process has been appropriately conducted is then confirmed. If the control computer 25 determines stoppering to be incomplete, the stoppering process retrial operation shown in FIG. 5C-(4), (5) is executed once again. This operation is repeated until the stoppering process has been completed for all the sample containers 3 present on the rack 1. After the stoppering process has been repeated any number of times set by the operator, if there is a sample container 3 determined not to be fully stoppered, appropriate information is output from the control computer 25 and at the same time the particular sample container 3 is returned to the retest sample storage unit 24 and undergoes processing by the operator.

The rack 1 that stoppering was finished is transferred to a sample storage unit 20.

Next, an operational flow of the stopper body hold mechanism 12 is described below using FIGS. 8A to 8H. The stopper body 5 that has been removed by the stopper body removing/mounting mechanism 4 is transferred from the destoppering position 2b to a stopper body loading position 22a of the stopper body hold mechanism 12 by the transport arm 4a of the stopper body removing/mounting mechanism 4. Embodiment shows that, when the transfer takes place, a hold area for the stopper body 5 is allocated to the stopper body hold unit (No. 2) 12a of the stopper body hold mechanism 12 by the control computer 25. The stopper body 5 is transferred to the position of stopper body hold unit (No. 2) 12a of the stopper body hold mechanism 12. The transferred stopper body 5, while it remains held in the stopper body hold unit (No. 2) 12a of the stopper body hold mechanism 12, stands by at that position until an unloading request has been issued from the control computer. The stopper body hold mechanism 12 includes a temperature control mechanism 12b and a moisture-retaining mechanism 12c to prevent the stopper body 5 from drying and suppress deterioration thereof due to changes in temperature, during the stand-by state. Upon a stoppering request occurring for the sample container 3 and the stopper body unloading request being issued from the control computer 25, the stopper body hold unit (No. 2) 12a of the stopper body hold mechanism 12 rotationally drives to a stopper body unloading position 22b and the stopper body removing/mounting mechanism 4 unloads the stopper body 5. This unloading process is not based upon first-in first-out processing only. The sample body 5 selected in accordance with a request from the control computer is unloaded. The stopper body 5 is transferred to the stoppering position 2d by the transport arm 4a of the stopper body removing/mounting mechanism 4 and then mounted on the sample container 3. After the stopper body 5 has been unloaded, the stopper body hold unit (No. 2) 12a is cleaned by the stopper body washing mechanism 23, then dried, and stands by until a transfer request for next stopper body 5 has occurred.

Figure 9:
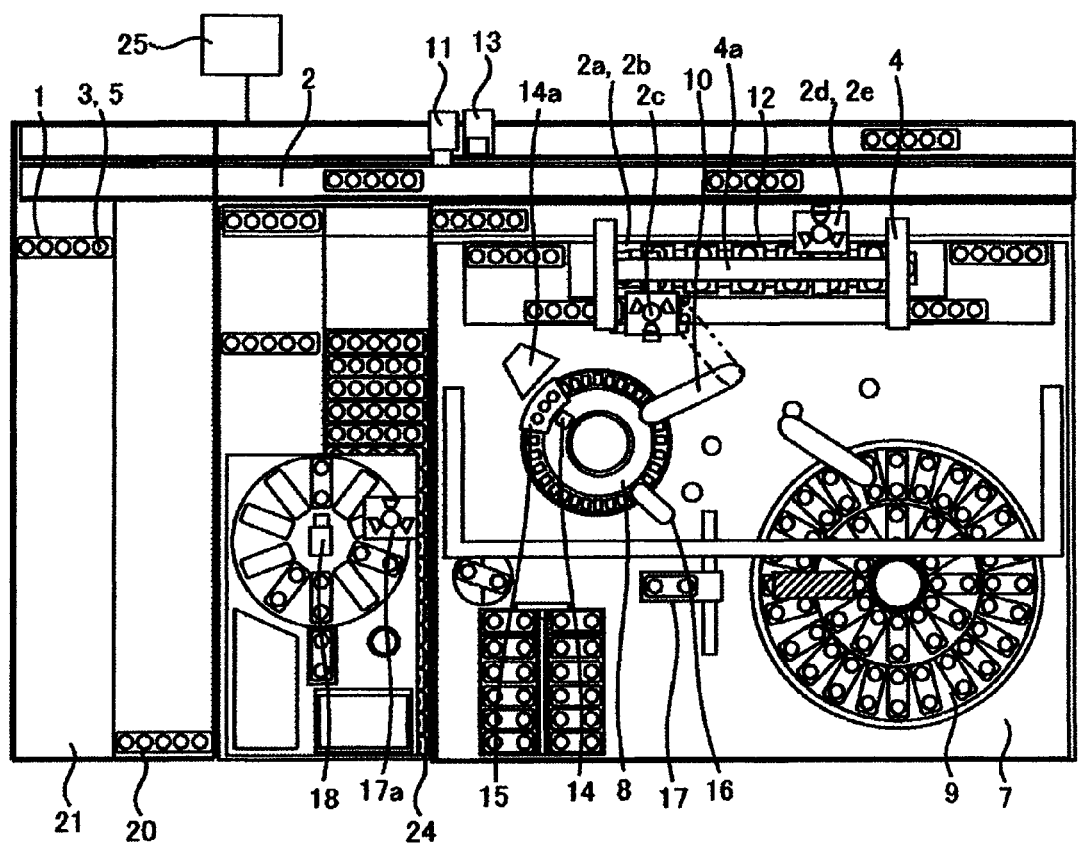
FIG. 9, which relates to a second embodiment of the present embodiment, is a schematic diagram showing an overall configuration of an automatic analysis system equipped with a mechanism for removing and mounting a stopper body for a sample container.

A second embodiment of the present invention is shown in FIG. 9.

FIG. 9 shows an example of a system configuration in which a stopper body removing/mounting mechanism 4 and a stopper body hold mechanism 12 are arranged around a sampling position 2c. Ideally, the configuration includes at least one stopper body chuck mechanism 4b at an upstream side of a sampling position 4c in order to remove a stopper body 5, and also includes at least one stopper body chuck mechanism 4b at a downstream side of the sampling position 4c in order to mount the stopper body 5. A destoppering position 2b and a stoppering position 2d can however be the same as the sampling position 2c.

Beneficial effects of the present embodiment having the above configuration are described below.

In a conventional technique, the dispensing of a sample and a reagent, associated with processes from the destoppering of a blood collection tube to the stoppering thereof, has required the gripping of the stopper body, which has been thought to cause a significant loss of time. Such a scheme has been unsuitable for continuous, efficient destoppering and stoppering of test tubes.

In another conventional technique, means that supplies a plurality of stoppers, one by one, is provided, in which case, test tubes can be stoppered both continuously and efficiently by holding each stopper from an upper surface and mounting the stopper on a corresponding test tube. A stopper that matches a sample container waiting for stoppering, however, has been unable to be mounted on the sample container by selectively picking the stopper from the above stand-by location. It has been impossible to reuse the stopper and reliably destopper and stopper the sample container.

In order to attain the object discussed above, in the present embodiment, a management system is included to supply to a sample container a stopper that has been removed from the sample container, and means that holds the stopper and stands by is also included. In addition, a stopper that matches the sample container waiting for stoppering is selectively picked from the stand-by location and mounted on this sample container. Stoppers can therefore be reused and sample containers can be reliably destoppered and stoppered.

DESCRIPTION OF REFERENCE NUMERALS

1 Rack
2 Transport mechanism
3 Sample container
4 Stopper body removing/mounting mechanism
5 Stopper body
6 Holder
7 Housing
8 Reaction disk
8a Reaction vessel
9 Reagent disk
9a Reagent probe
10 Sample probe
11 Sample information reading mechanism
12 Stopper body hold mechanism
12a Stopper body hold unit
13 Stopper body identification mechanism
14 Light source
14a detection Optical device
15 Container washing mechanism
16 Stirrer
17 Reagent container hold mechanism
18 Reagent container information reading mechanism
19 Stopper body protecting mechanism
20 Sample storage unit
21 Sample loading unit
22 Stopper body loading/unloading position
23 Stopper body washing mechanism
24 Retest sample storage unit
25 Control computer

The invention claimed is:

1. An automatic analysis system equipped with a mechanism to transport a sample container having a stopper body, the system comprising:
a sample dispensing mechanism that dispenses a predetermined amount of sample accommodated in the sample container;
a destoppering mechanism that removes the stopper body from the sample container at a stopper removing position;
a control unit that stores therein association between the sample container and the stopper body of the sample container;
a stoppering mechanism that in accordance with the association stored into the control unit, mounts the stopper body back on the sample container containing the sample dispensed by the sample dispensing mechanism; and
a stopper body transport mechanism that transports the stopper body that the destoppering mechanism has removed at the stopper removing position to a stopper mounting position.

2. The automatic analysis system according to claim 1, wherein:
the stopper body transport mechanism includes a stopper body hold mechanism that holds a plurality of stopper bodies removed by the destoppering mechanism.

3. The automatic analysis system according to claim 2, wherein the stopper body hold mechanism includes all or part of:
a mechanism that controls a temperature of the stopper body;
a stopper body moisturizing mechanism that prevents the stopper body from drying; and
a mechanism that cleans the stopper body.

4. The automatic analysis system according to claim 1, further comprising:
a stopper body identification mechanism that identifies the stopper body of the sample container; and wherein
the destoppering mechanism or the stoppering mechanism can switch between a destoppering operation for removing the stopper body from the sample container, and a stoppering operation for mounting the stopper body on the sample container.

5. The automatic analysis system according to claim 1, further comprising:
a first identification mechanism that identifies both of the stopper body removed by the destoppering mechanism, and the sample container from which the stopper body has been removed; and
a second identification mechanism that identifies both of the stopper which the destoppering mechanism is to mount, and the sample container on which the stopper body to be mounted.

6. The automatic analysis system according to claim 5, wherein:
the stopper body transport mechanism includes a stopper body hold mechanism that holds a plurality of stopper bodies removed by the destoppering mechanism:
the stopper body transport mechanism that transports to the stoppering mechanism any stopper body selected in association with identification results received from the first identification mechanism and the second identification mechanism.

7. The automatic analysis system according to claim 5, wherein:
the first identification mechanism or the second identification mechanism identifies a kind, height, and diameter of the sample container, a kind, color, existence of the stopper body, and a positioning code of the stopper body.

8. The automatic analysis system according to claim 1, wherein:
the destoppering mechanism conducts a destoppering process by use of a stopper body protecting mechanism that fits the stopper body or the stoppering mechanism conducts a stoppering process by use of a stopper body protecting mechanism that fits the stopper body.

9. The automatic analysis system according to claim 1, further comprising:
   a destoppering identification mechanism that determines a state of destoppering in the destoppering mechanism; and
   a stoppering identification mechanism that determines a state of stoppering in the stoppering mechanism.

10. The automatic analysis system according to claim 1, further comprising:
    an unloading mechanism that unloads a sample container unsuccessfully destoppered in the destoppering mechanisms or stoppered in the stoppering mechanism; and
    a retest sample storage mechanism for storage of the sample container unloaded from the unloading mechanism.

* * * * *